United States Patent

Malek et al.

[11] Patent Number: 5,837,195
[45] Date of Patent: Nov. 17, 1998

[54] LUMINOMETER

[75] Inventors: Michael L. Malek, North Olmstad; Glen A. Carey, Grafton; Gregory A. Coghlan, Elyria, all of Ohio

[73] Assignee: Chiron Diagnostics Corporation, E. Walpole, Mass.

[21] Appl. No.: 826,895

[22] Filed: Apr. 9, 1997

Related U.S. Application Data

[62] Division of Ser. No. 502,005, Jul. 13, 1995, Pat. No. 5,686,046.

[51] Int. Cl.⁶ .................................................. G01N 21/76
[52] U.S. Cl. ......................... 422/52; 422/64; 422/82.08; 436/48; 250/361 C
[58] Field of Search .......................... 422/52, 64, 82.08, 422/105, 109; 250/361 C, 361 R, 458.1, 461.1; 436/45, 48, 172; 356/39

[56] References Cited

U.S. PATENT DOCUMENTS

| | | |
|---|---|---|
| 3,520,660 | 7/1970 | Webb . |
| 3,726,599 | 4/1973 | Neary ....................................... 356/246 |
| 3,998,592 | 12/1976 | Pyle . |
| 4,190,368 | 2/1980 | Etess ..................................... 250/361 C |
| 4,406,547 | 9/1983 | Aihara ..................................... 356/414 |
| 4,472,352 | 9/1984 | Quesneau et al. ......................... 422/52 |
| 4,563,331 | 1/1986 | Losee et al. ............................... 422/52 |
| 4,755,055 | 7/1988 | Johnson et al. ............................ 422/52 |
| 4,785,407 | 11/1988 | Skagami . |
| 4,863,690 | 9/1989 | Berthold et al. ........................... 422/52 |
| 5,653,940 | 8/1997 | Carey et al. ............................... 422/52 |

FOREIGN PATENT DOCUMENTS

| | | |
|---|---|---|
| 0038134 | 10/1981 | European Pat. Off. . |
| 0226374 | 6/1987 | European Pat. Off. . |
| 0502638 | 9/1992 | European Pat. Off. . |
| 0580141 | 1/1994 | European Pat. Off. . |
| 0616208 | 9/1994 | European Pat. Off. . |
| 8303138 | 9/1983 | WIPO . |
| 9004775 | 5/1990 | WIPO . |
| 9309420 | 5/1993 | WIPO . |

OTHER PUBLICATIONS

Pronko, J.G. and Chapman I.V., *Microcomputer–controlled Chemiluminescence Spectrometer for Solid Phase Samples* Review of Science Instruments. 57 (2), Feb., 1986, pp. 191–196.

*Primary Examiner*—Jeffrey Snay
*Attorney, Agent, or Firm*—Arthur S. Morgenstern; Charles L. Gagnebin, III; Robert P. Blackburn

[57] ABSTRACT

A luminometer for determining the composition of a specimen sample includes an annular guide path for sample containing cuvettes within a light tight housing. A rotor moves spaced segments through the guide path with the cuvettes positioned between the segments. The luminometer further includes one or two detector assemblies coupled to the housing and positioned to view and detect light emitted by cuvettes as they pass along the guide path between segments. A cuvette is advanced around the housing via the rotor and rotor segments and when the cuvette reaches a predetermined position on the housing, a reagent, such as a base, is added to the cuvette to initiate a chemiluminescent reaction within the cuvette and provide an emission of light energy in a predetermined spectral range. The luminometer has a waste aspiration probe to remove the contents of the cuvette after it passes the detector. A cuvette elevator moves a sample containing cuvette into the guide path between segments and an exit chute removes cuvettes after their contents have been aspirated. The luminometer permits continuous uninterrupted sample testing when coupled to an incubation chamber in which the cuvettes receive samples and test specific reagents before they are moved into the luminometer by the elevator.

4 Claims, 9 Drawing Sheets

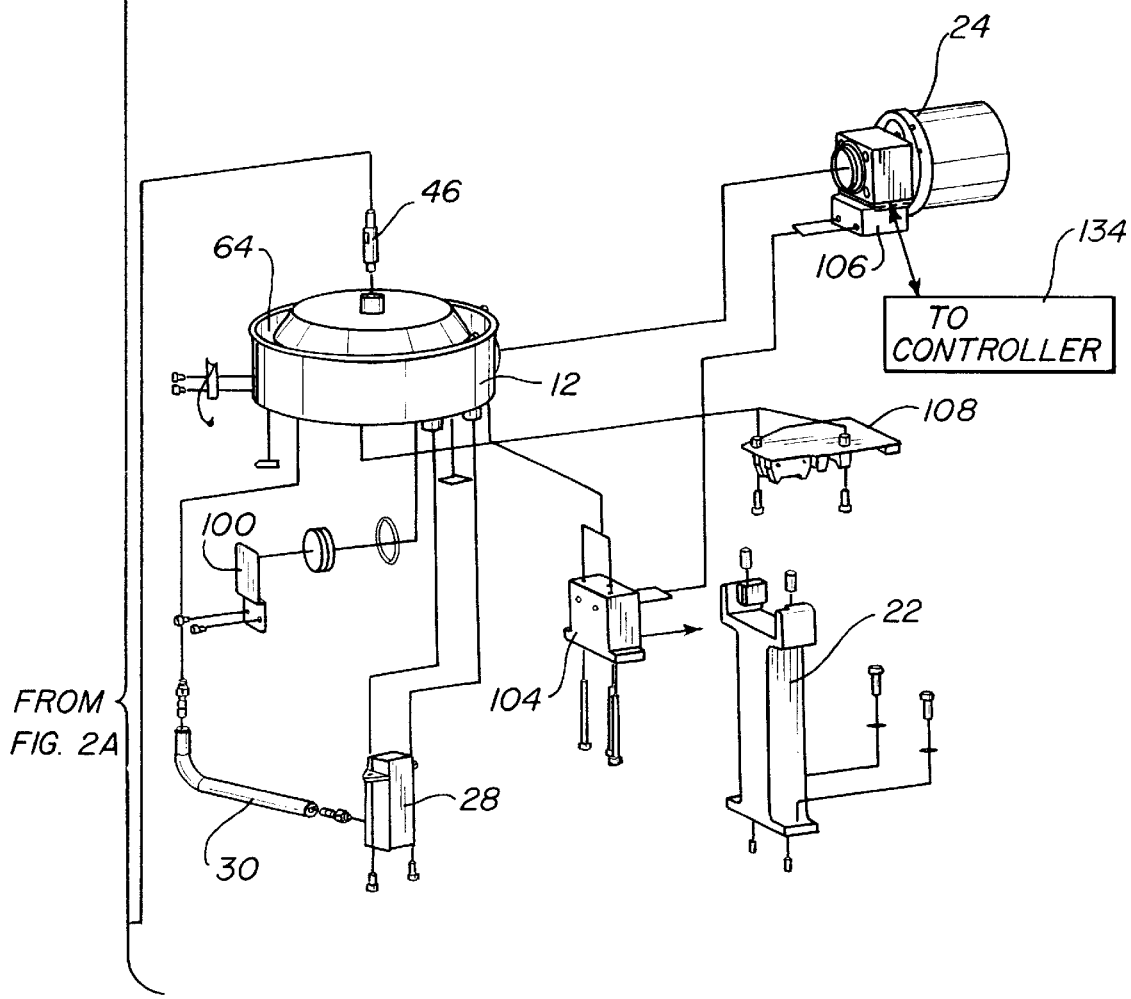

LUMINOMETER

This is a divisional of copending application(s) Ser. No. 08/502,005 filed on Jul. 13, 1995, now issued as U.S. Pat. No. 5,686,046.

FIELD OF THE INVENTION

This invention relates to specimen testing apparatus and more particularly to luminometers.

BACKGROUND OF THE INVENTION

As is known in the art, systems used to test specimen samples such as blood samples, for example, add a reagent to the sample in a cuvette The reagent molecules reacts with and bind to certain components in the sample. The remainder of the sample is normally removed and a further reagent such as a base is added to cause parts of the bound molecules to luminesce. The reagent reaction time is normally an important parameter of the testing and incubation within strict time limits is required before a reacted sample is ready for luminescence detection. The intensity and spectral distribution of the emitted light is indicative of the concentration of the sample component being tested for. The light emissions may be fed through a spectral filter before application to the detector. Thus, with knowledge of the type of specimen sample, the type of reagent and the resultant spectral representation it is possible to determine the presence of certain chemicals in the specimen sample. Separate tests may be run with different reagents in the separate chambers to test for other constituents in the specimen.

As is also known, it is desirable to minimize the amount of background light which enters the measurement region of the luminometer. By minimizing the amount of background light from a luminescent signal which is descriptive of a sample's constituent concentration, assay results may be refined.

The testing of samples to be done efficiently in a hospital or clinical environment requires a large throughput of samples per hour. Any parts of a test system that require shutdown of the test sequence impairs the efficiency and can result in wasted tests if time limits are exceeded.

SUMMARY OF THE INVENTION

Thus according to the present invention, precise and efficient, continuous light emission detection in a system for specimen analysis is achieved with a luminometer according to the invention. A luminometer for determining the composition of a specimen sample includes an annular guide path for sample containing cuvettes within a light tight housing. A rotor moves spaced segments through the guide path with the cuvettes positioned between the segments. The luminometer further includes one or two detector assemblies coupled to the housing and positioned to view and detect light emitted by cuvettes as they pass along the guide path between segments. A cuvette is advanced around the housing via the rotor and rotor segments and when the cuvette reaches a predetermined position on the housing, a reagent, such as a base, is added to the cuvette to initiate a chemiluminescent reaction within the cuvette and provide an emission of light energy in a predetermined spectral range. The luminometer has a waste aspiration probe to remove the contents of the cuvette after it passes the detector. A cuvette elevator moves a sample containing cuvette into the guide path between segments and an exit chute removes cuvettes after their contents have been aspirated. The luminometer permits continuous uninterrupted sample testing when coupled to an incubation chamber in which the cuvettes receive samples and test specific reagents before they are moved into the luminometer by the elevator.

Furthermore, in those applications where it may be desirable to provide a system in which a plurality of reagents are added to a single cuvette and a detection system must simultaneously detect light emission in a plurality of different spectral ranges, this is accommodated in the present invention by the provision of a second light detection assembly.

The housing includes a recess region formed by a base wall having inner and outer side walls projecting from a first surface therefore. The recess region follows a continuous path around a perimeter of the housing. The housing includes an entrance chute through which a cuvette is disposed by the elevator and retained in the recess region of the housing between segments of the rotor. The rotor advances the cuvette along the recess to a predetermined location in the housing for the addition of a chemiluminiscence inducing material such as a base. The one or two detector assemblies are disposed on opposite sides of the guide path in the housing. In accordance with this particular arrangement, a luminometer capable of detecting the composition of a specimen sample having a resultant luminescence in one or more separate spectral ranges is provided.

The detector assemblies may include, for example, photomultiplier tubes (PMTs). Each of the PMTs may substantially simultaneously provide a response to a chemiluminescent flash produced in the reaction vessel. A filter may be placed in the light path for each PMT such that a first one of the PMTs may respond to light emissions in a first spectral range and a second one of the plurality of PMTs may substantially simultaneously respond to light emissions in a second spectral range. Thus, the luminometer may detect, in a single test, light emissions in two different spectral ranges reflective of two separate sample components being tested for.

In one embodiment, the base portion of the housing recess region has a guide channel provided therein. A rotor segment having a boss on a bottom surface thereof is disposed in the recess region of the housing. The rotor segment and guide channel together form a light trap.

A temperature control circuit coupled to the detector assembly maintains the temperature of the detector assembly within a predetermined temperature range. Thus, the detectors provide consistent measurement values with minimum measurement drift over a period of time.

BRIEF DESCRIPTION OF THE DRAWINGS

The foregoing features of this invention as well as the invention itself may be more fully understood from the following detailed description of the drawings in which:

FIGS. 2A, 2B and 2C are exploded views of the luminometer of FIGS. 1A AND 1B;

DESCRIPTION OF THE PREFERRED EMBODIMENTS

Figure 1A:
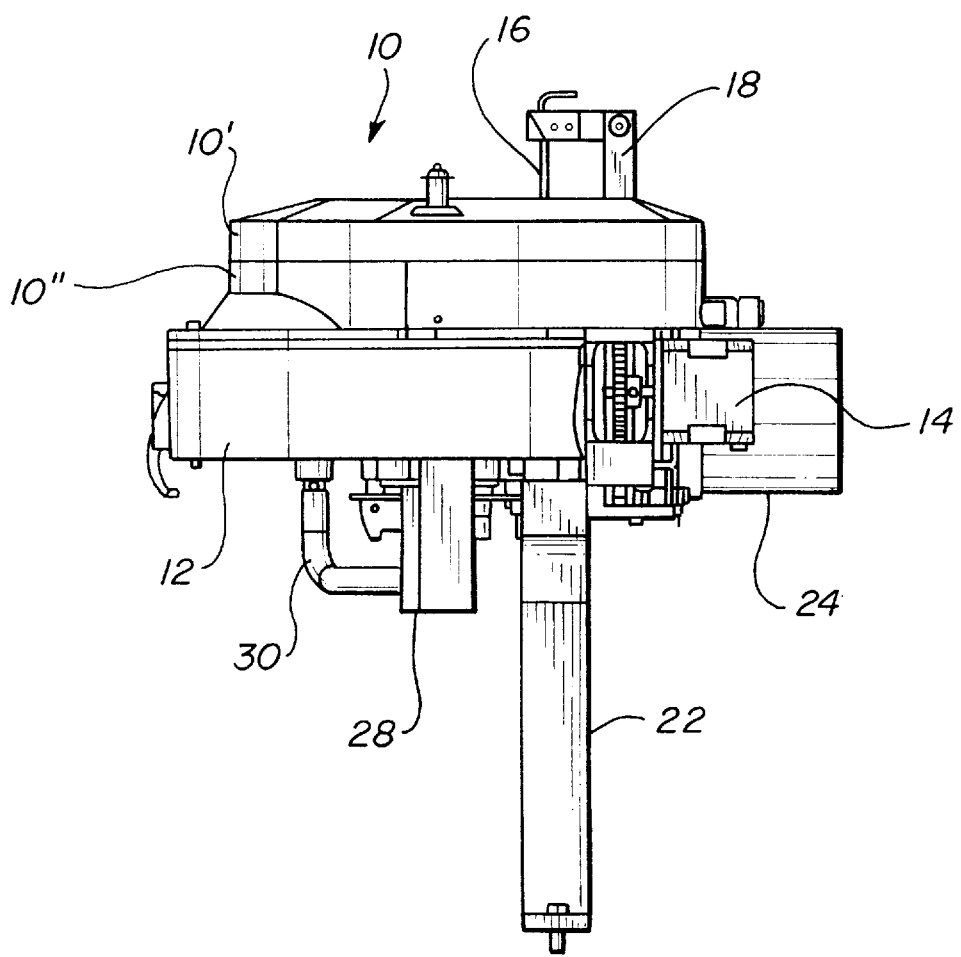
FIG. 1A is a side view of a luminometer assembly.
Figure 1B:
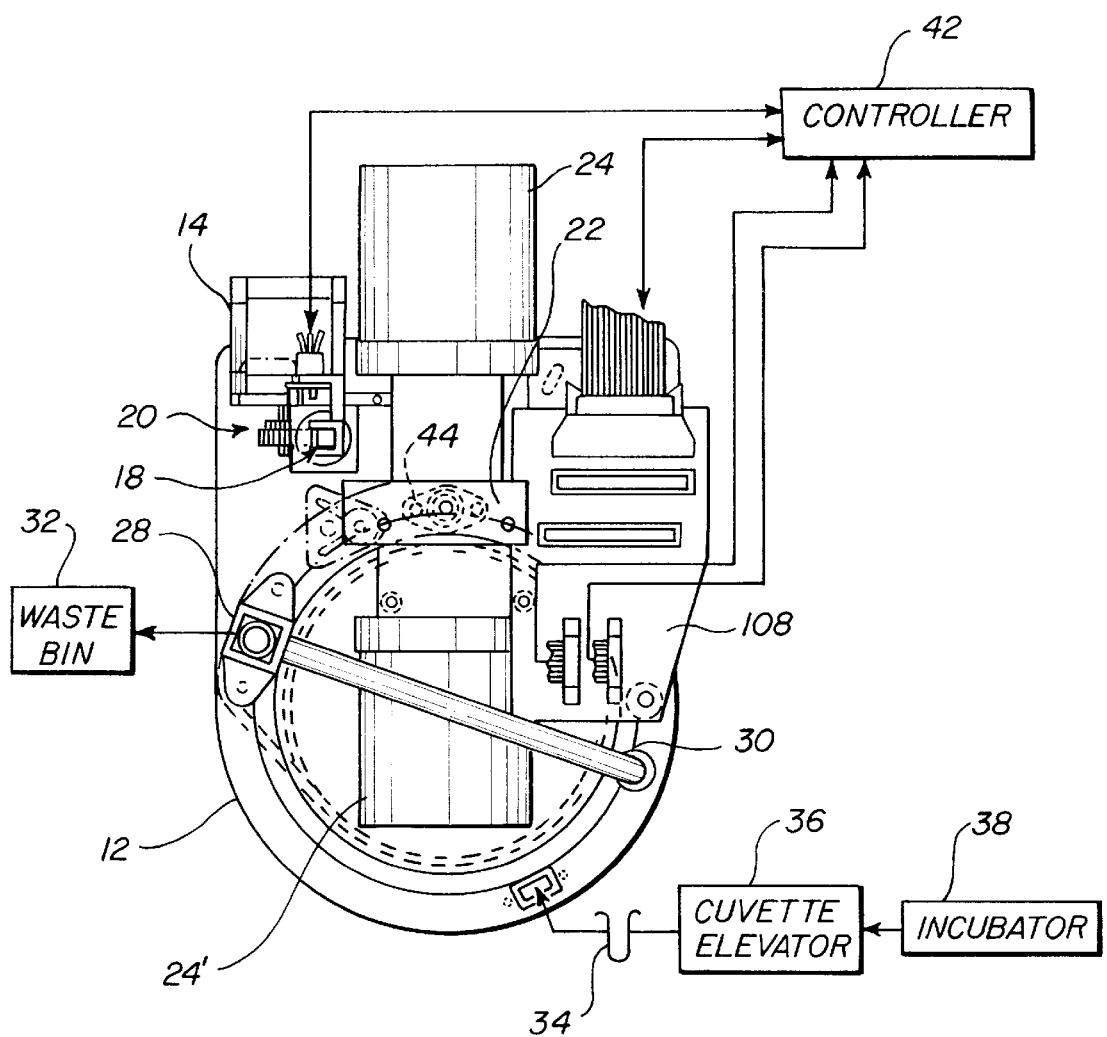
FIG. 1B is a bottom view of the luminometer assembly of FIG. 1A including control electronics.

Referring now to FIGS. 1A and 1B there is shown a luminometer according to the present invention having housing comprising a top cover 10, having upper and lower portions 10' and 10" and bottom guide path housing 12 through which the cuvettes containing samples being tested are moved. A waste aspirate probe assembly 14 controls a waste aspirate probe 16 on an arm 18 raised and lowered by a rack and pinion mechanism 20 to remove waste fluid after luminescence detection described below.

The luminometer is supported on a pillar 22, typically from a structure having an incubation system for sample testing. Pillar 22 acts as a heat sink for TED's described later. A detector assembly 24 is also supported on the pillar 22 to position the detector and PMT therein to view cuvettes as they are positioned at appropriate viewing stations in the guide path of housing 12 as described below. A second detector assembly 24' similar to assembly 24 can be provided on the other side of the pillar 22 within a hollow interior of the guide path housing 12. The cuvettes in the space viewed by the detector assemblies 24, 24' are provided with a luminescence inducing chemical through an aperture 44 above the cuvette in the station by the detector assemblies 24, 24'.

An ejection chute 28 is provided below a position on the housing 12 where the cuvettes are moved to in the guide path after passing past the detector assembly 24. An aperture in the bottom of the guide path in the housing 12 allows the cuvette to drop and a conduit 30 acts as a preventative drain to remove base leakage from the channel 64 to the chute 30 and prevent it getting to the entrance aperture.

Cuvettes 34 enter the housing 12 through a bottom aperture via an elevator 36 from an incubation system 38 which may be as shown in commonly owner co-pending application Ser. No. 08/338,022, filed Nov. 10, 1994, now U.S. Pat. No. 5,599,501. A controller 42 provides control signals to the luminometer and receives data from the luminometer for control and representative of sample testing.

Figure 2A:
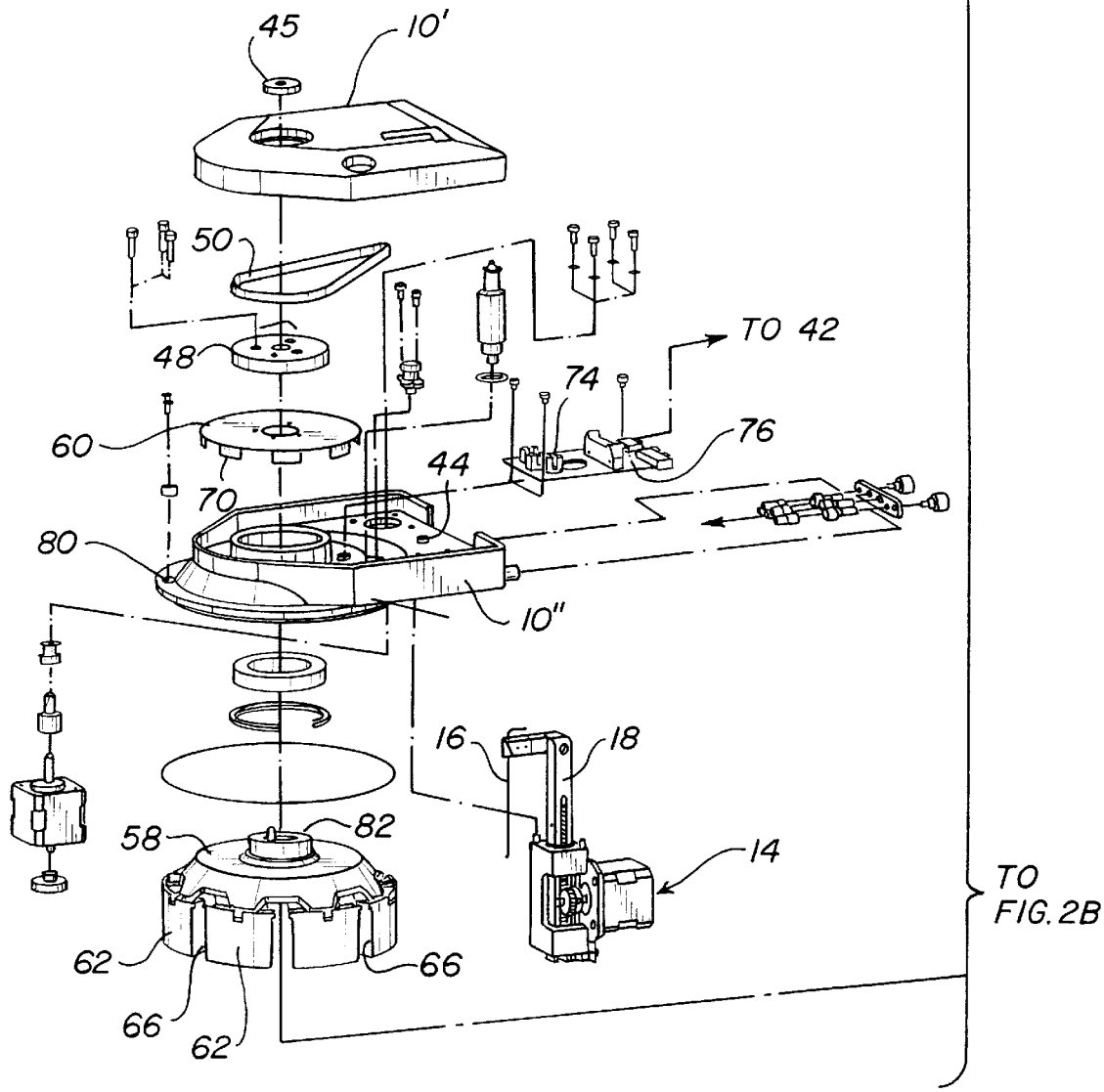
Figure 2C:
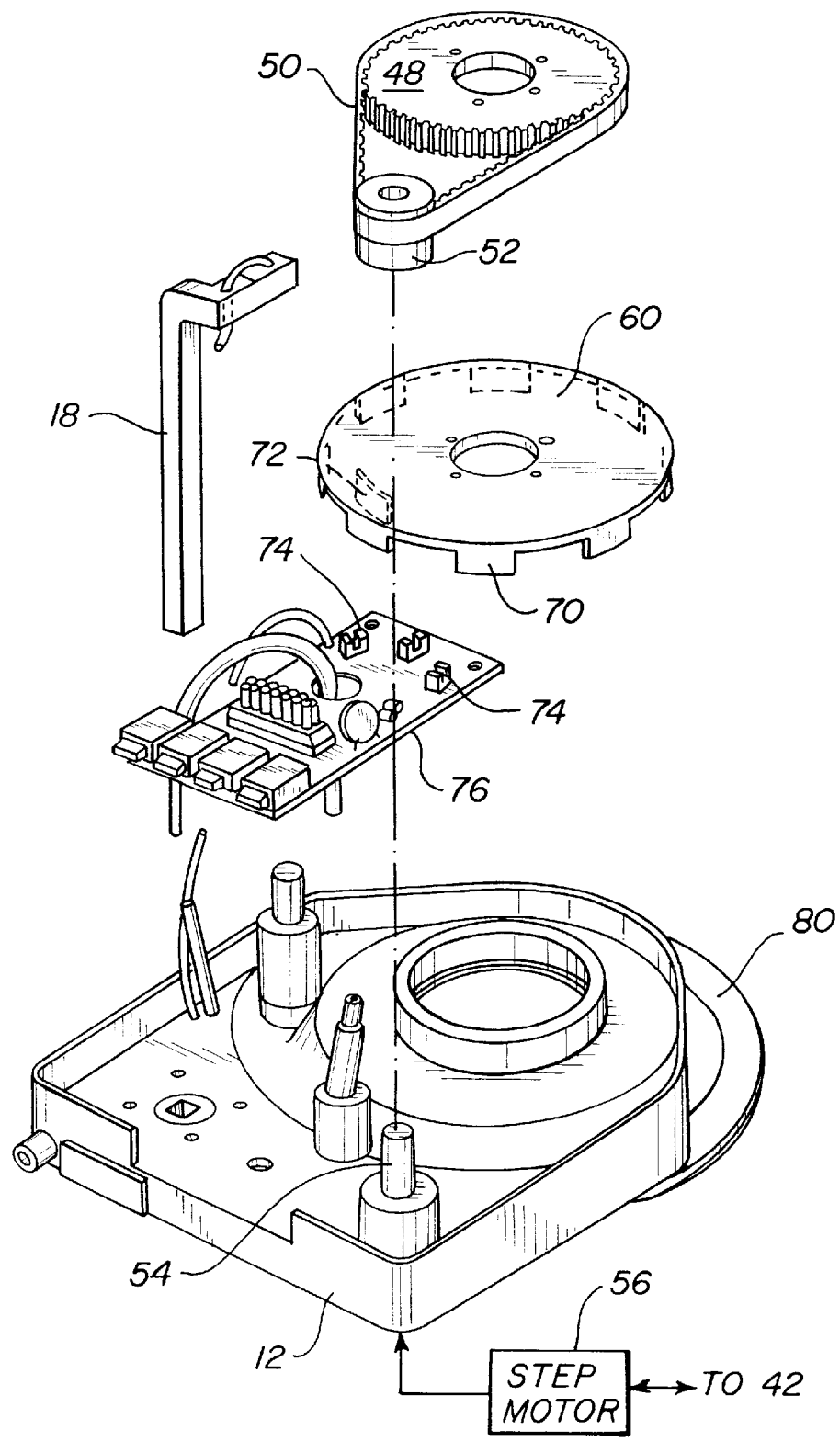

As further shown in FIGS. 2A–C the internal structure of the luminometer is shown. The cover portions 10' and 10" are held to each other and to the housing 12 by a nut 45 that tightens onto a shaft 46 set into the center of the housing 12. Under upper portion 10', a pulley 48 is driven by a belt from a further pulley 52 on a shaft 54 turned by a motor 56 by signals from controller 42. The pulley 48 in turn drives a rotor 58, coupled through an optical encoder disc 60 that is keyed to the rotor 58. The rotor 58 has plural segments 62 (in this case 8) that are floatingly attached to the rotor and that run in a channel 64 defining the guide path of the housing 12. The segments 62 are positioned by rotor 58, creating slots 66 that capture cuvettes as they are moved into the guide path between the segments 62 under control by controller 42 as the cuvettes are moved up by elevator 36.

The encoder disc has vanes 70 and a master vane 72 that pass optical sensors 74 on a PC board 76 with the resulting position signals sent to controller 42 to stop the rotor 58 at appropriate positions for the cuvettes to be loaded from elevator 36, positioned for viewing by a detector assembly, for fluid aspiration by probe 16, and for ejection through chute 28. A covered viewing port 80 allows alignment of the luminometer for proper cuvette loading when assembled at an incubation system.

The rotor 58 is journaled in a bearing 82, between housing 12 and rotor 58. A shaft 46 from housing 12 passes freely through the bearing 82. A large diameter single bearing provides desired rigidity and stability to the rotor. The cover portion 10" seals the guide path of channel 64 from the light environment to insure that there is a minimum chance of light from outside reaching the viewing station for the detector assemblies 24, 24'.

Figure 3:
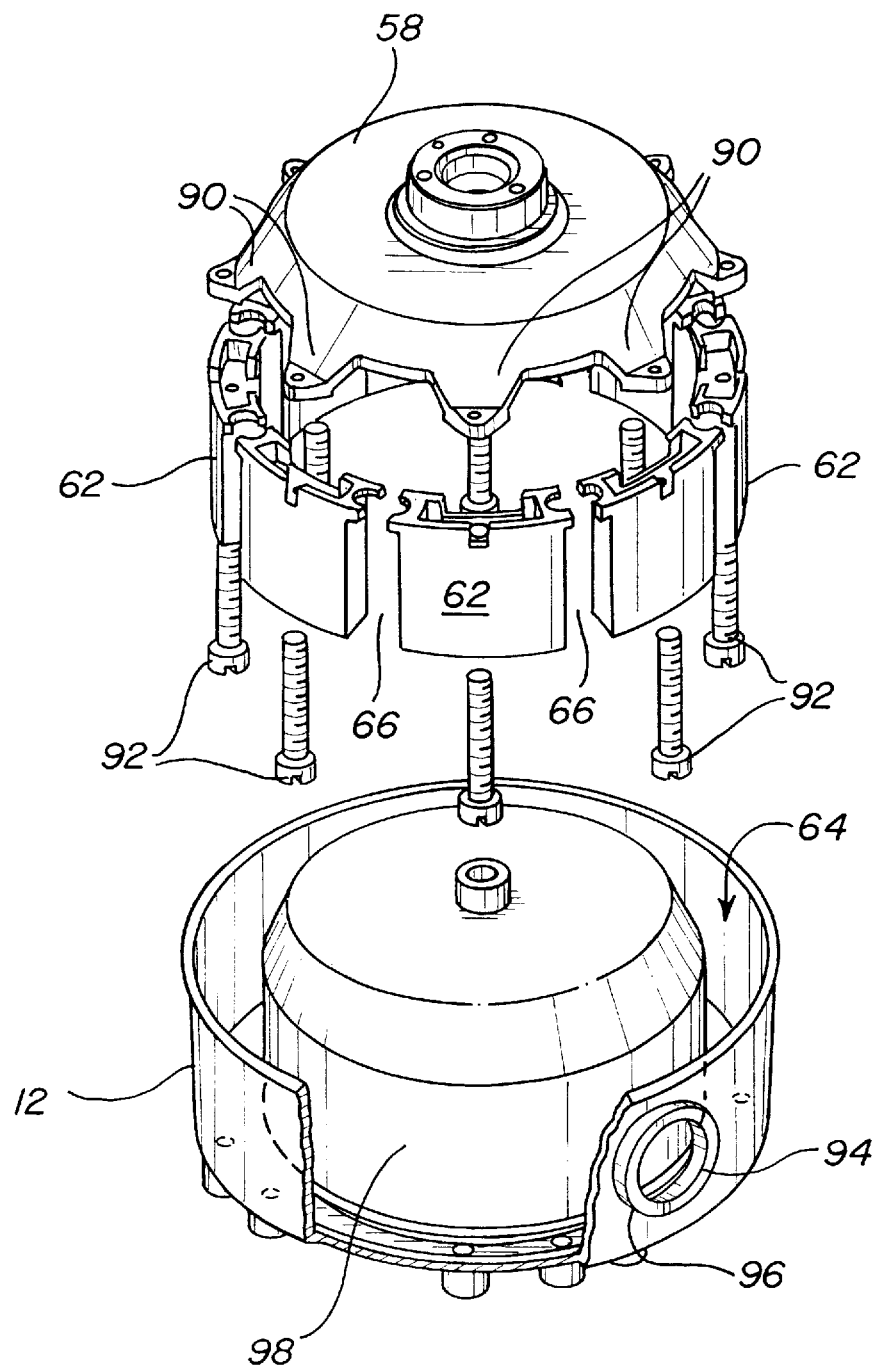
FIG. 3 is a side exploded view of a luminometer rotor, segments and segment guide path housing.

As shown in FIG. 3, the segments 62 are fastened to the rotor 58 at arms 90 by shoulder screws 92 on which the segments ride. These allow the segments to float slightly up and down and in and out and rotate about the screw axis preventing binding and maintaining constant cuvette spacing. This coupling avoids jamming of the segments and cuvettes as they rotate in the channel 64 along the guide path. The housing 12 is fabricated of a graphite plastic composite to allow some electrical conduction and avoid the build up of static charge from the motion of the parts.

The view of FIG. 2B shows a single detector assembly 24 fitted in an aperture 94 of an exterior wall 96 of housing 12. Preferably a similar aperture 94' (see FIG. 4 below) is fitted in interior wall 98 of housing 12 to accommodate a plate 100 and plug 102 for use with the single detector assembly 24. Plate 100 and detector assembly 24 are mounted to heat sink pillar 22 via support blocks 104 and 106. A PC board 108 accommodates connectors for electrical connection between the luminometer and the controller 42. Various unnumbered fastening screws, washers, and rings are shown in the figures discussed above to provide conventional attachments of parts as noted.

Figure 4:
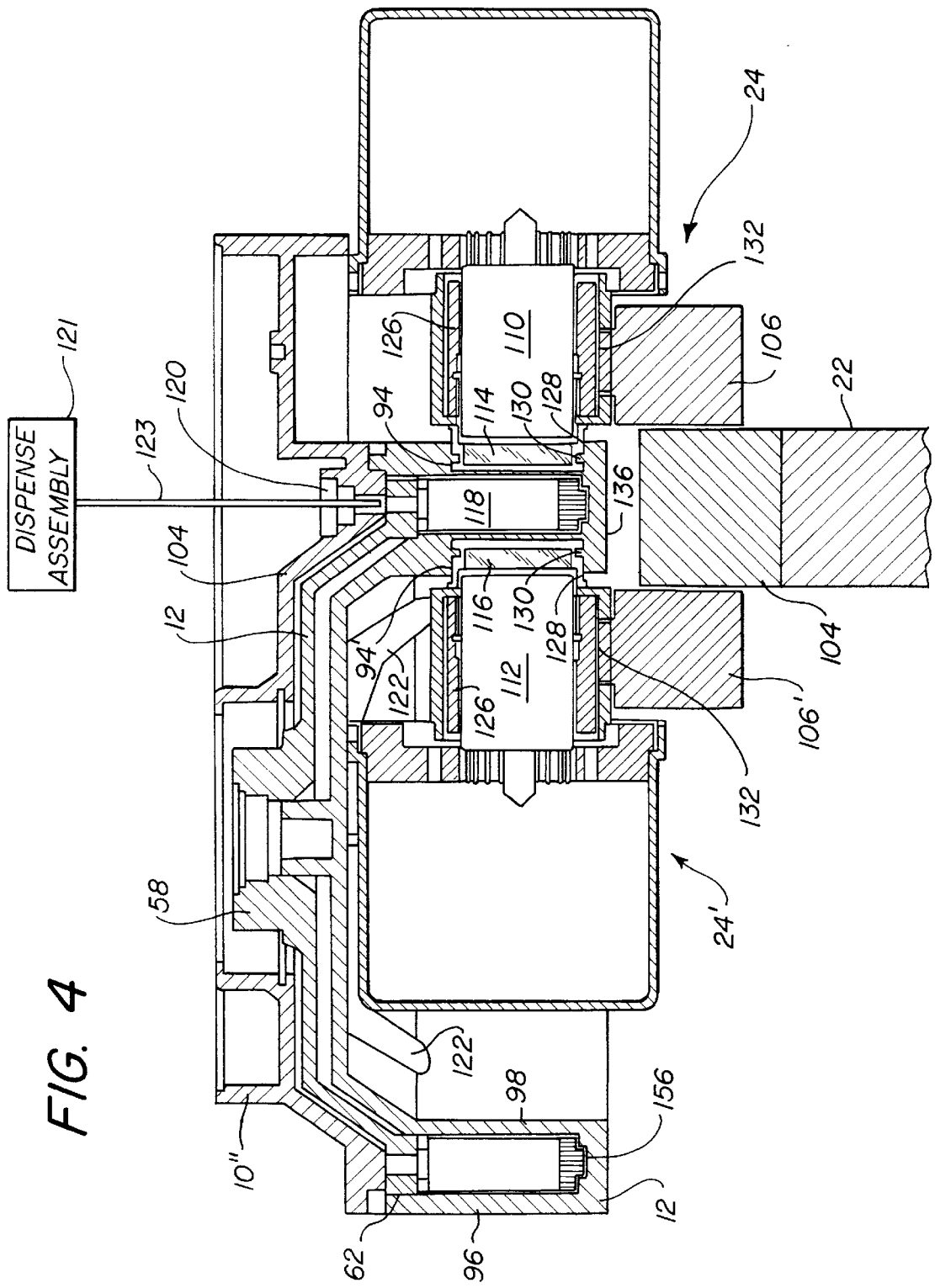
FIG. 4 is a sectional view of a luminometer rotor assembly and PMT detector assemblies.

FIG. 4 shows an embodiment in which there are two detectors 24, 24' for the detection of typically plural frequencies of light emission from the cuvette. The two detectors are set in respective apertures 94 and 94' in housing walls 96 and 98. Each houses respective PMTs 110 and 112 viewing, through lenses 114 and 116, a region 118 of the guide path for cuvettes in channel 64 at which the cuvettes stop for administration of a emission inducing reagent such as a base via a dispense assembly 121 and a probe 123 for injecting base through a seal 125 in an aperture 120 in housing 12 and cover portion 10", while maintaining a light tight seal. The interior of housing 12, within walls 98, is strengthened by struts 122.

The PMTS 110, 112 are surrounded by thermal sleeves 126 and set in lens caps 128 that fit into the apertures 94, 94' with O-rings in grooves 130. The thermal sleeves 126 are mounted to thermo electric devices (TEDs) 132 that are controlled by controller 134 (FIG. 2B) for maintaining a consistent operating temperature to the PMTS, such as 25° C. ±1.25° C., and their environment.

Figure 5A:
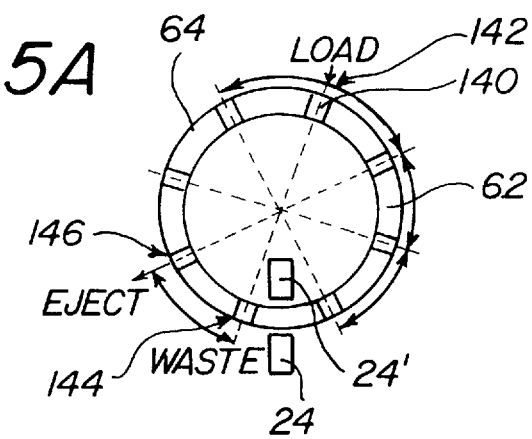
FIGS. 5A–C are views of the operational positions of the rotor in the operation of the luminometer.
Figure 5B:
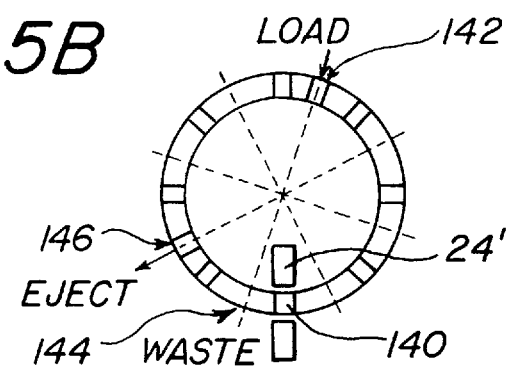
Figure 5C:
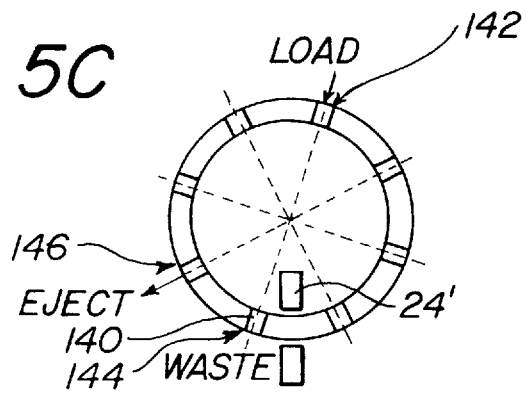

In operation under the control of controller 42, as shown in FIGS. 5A–C, a cuvette is loaded into the luminometer guide path of channel 64 at load station 143 via the elevator 36 to sit in a space 140 between adjacent ones of the segments 62. At the same or nearly the same time, the fluid in the cuvette which has just passed the detectors 24, optionally including detector 24', is aspirated at a waste station 144 through aspirate probe tube 18. Similarly, the next along cuvette is ejected at an eject station 146 into the chute 28 to waste bin 32. Several repetitions of this sequence later, the cuvette in space 140 is rotate along the guide path in channel 64 to be in the view of the one or two detectors and their respective PMTs where base is added and a precise time later the luminescence is measured. The space 140 then passes to the waste station 144 for aspiration of its contents into a waste container and subsequently is moved to the eject station 146 all the while that further respective cuvettes are passing through the sequence of being loaded, chemiluminesced with base, light detected and aspirated as described above.

Figure 6A:
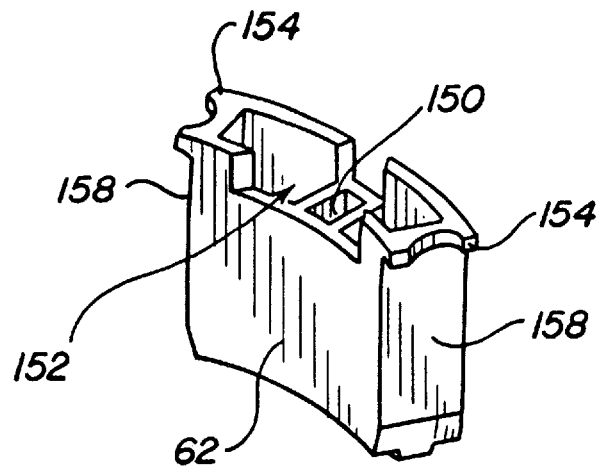
FIGS. 6A–C are views of segments for the rotor of FIGS. 4 and 5 and their alternatives.
Figure 6B:
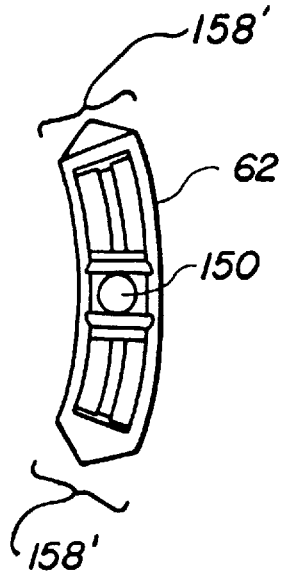
Figure 6C:
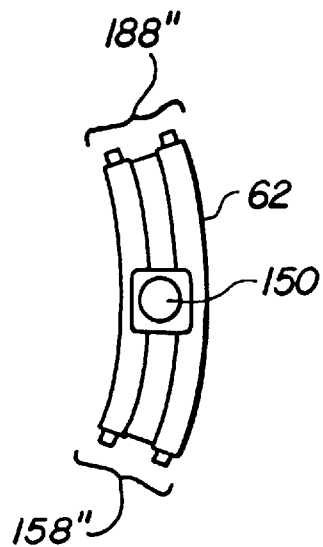

The segments 62 are illustrated more fully in FIGS. 6A–B where they are shown to include a central bore to accommodate the screws 92 and a recess region 152 that accommodates the arms 90 (FIG. 3). Upper flanges 154 keep the cuvettes positioned thereunder, the bottoms of the cuvettes being held by the grooved bottom 156 (FIG. 4) of the housing channel 64. The ends 158 of the segments 62 which bear against the cuvettes as they are moved along the guide path of the channel 64 can be chamfered as shown at 158' in FIG. 6B to reflect chemiluminescence light back toward the PMTs of the detectors 24, 24'. Alternatively, the ends can be configured with bumps that create minimal contact between the cuvettes and the segments to minimize the effects of sticking.

Having described preferred embodiments of the invention, it will now become apparent to one of skill in the art that other embodiments incorporating the concepts may be used. It is felt, therefore, that these embodiments should not be limited to disclosed embodiments but rather should be limited only by the spirit and scope of the appended claims.

What is claimed is:

1. A luminometer comprising:

a rotor having a plurality of rotor segments suspended in spaced relationship below the rotor;

the rotor segments having first and second opposing ends and first and second opposing surfaces and a bore between the first and second opposing surfaces of said rotor segment;

a coupling suspending each said rotor segment to said rotor;

a housing having a channel through which are moved sequentially plural sample containers and having an aperture provided therethrough into said channel, and rotatably supporting the rotor so as to suspend the segments in said housing channel along which said segments travel with rotation of said rotor;

said coupling accommodating segment motion within said channel to provide limited motion that maintains consistent spacing between opposing ends of adjacent segments and avoids binding in said channel wherein said spacing is sufficient to support a sample container between said adjacent segments;

sample load, test and removal stations along the channel;

a detector coupled to said housing and disposed through the aperture to detect light emitted from a predetermined region of the channel of said housing; and a temperature detection and control circuit coupled to said detector.

2. The luminometer of claim 1 wherein said detector further comprises:

a PMT in a thermal insulating sleeve; and a TED coupled to said PMT thermal sleeve.

3. The luminometer of claim 1 further comprising:

a second detector coupled to said housing on an opposite side of said channel from said first mentioned detector; and said temperature control circuit coupled to said first and second detectors.

4. The luminometer of claim 3 wherein said second detector further comprises:

a PMT in a thermal insulating sleeve; and a TED coupled to said PMT thermal sleeve and controlled by said control circuit.

* * * * *